US011318022B2

(12) United States Patent
Brazil

(10) Patent No.: US 11,318,022 B2
(45) Date of Patent: May 3, 2022

(54) KNEE PROSTHESIS TIBIAL COMPONENTRY HAVING INTERCHANGEABLE COMPONENTS

(71) Applicant: SIGNATURE ORTHOPAEDICS EUROPE LTD, Dublin (IE)

(72) Inventor: Declan Brazil, Lane Cove West (AU)

(73) Assignee: SIGNATURE ORTHOPAEDICS EUROPE LTD, Dublin (IE)

( * ) Notice: Subject to any disclaimer, the term of this patent is extended or adjusted under 35 U.S.C. 154(b) by 0 days.

(21) Appl. No.: 17/273,682

(22) PCT Filed: Sep. 6, 2019

(86) PCT No.: PCT/AU2019/050957
§ 371 (c)(1),
(2) Date: Mar. 4, 2021

(87) PCT Pub. No.: WO2020/047608
PCT Pub. Date: Mar. 12, 2020

(65) Prior Publication Data
US 2021/0330466 A1    Oct. 28, 2021

(30) Foreign Application Priority Data
Sep. 6, 2018  (AU) ............... 2018903316

(51) Int. Cl.
*A61F 2/38*     (2006.01)
*A61F 2/30*     (2006.01)

(52) U.S. Cl.
CPC .... *A61F 2/389* (2013.01); *A61F 2002/30331* (2013.01); *A61F 2002/30481* (2013.01); *A61F 2002/30616* (2013.01)

(58) Field of Classification Search
CPC . A61F 2/389; A61F 2/3868; A61F 2002/3031
See application file for complete search history.

(56) References Cited

U.S. PATENT DOCUMENTS

| 7,628,818 | B2 | 12/2009 | Hazebrouck et al. |
| 2008/0114464 | A1 | 5/2008 | Barnett et al. |
| 2011/0029090 | A1 | 2/2011 | Zannis et al. |
| 2011/0035017 | A1 | 2/2011 | Deffenbaugh et al. |
| 2013/0184829 | A1 | 7/2013 | Wyss et al. |

FOREIGN PATENT DOCUMENTS

WO    2016026007 A1    2/2016

OTHER PUBLICATIONS

International Search Report & Written Opinion dated Oct. 17, 2019 from PCT Application No. PCT/AU2019/050957.

*Primary Examiner* — Jason-Dennis N Stewart
(74) *Attorney, Agent, or Firm* — Innovation Capital Law Group, LLP; Vic Lin

(57) ABSTRACT

Knee prosthesis tibial componentry has a bearing insert defining a superior condyle articular surface and a planar inferior bearing surface. A tray having a platform defining a superior bearing surface and an inferior stem engages the insert. The tray has a quadrant of retention buttresses having anterior and posterior buttresses, each extending superiorly with respect to the superior bearing surface and extending in from a peripheral edge of the superior bearing surface. The insert has a quadrant of respective spaced apart retention recesses having anterior and posterior recesses, each recessed superiorly with respect to the inferior bearing surface and extending in from a peripheral edge of the inferior bearing surface.

21 Claims, 5 Drawing Sheets

KNEE PROSTHESIS TIBIAL COMPONENTRY HAVING INTERCHANGEABLE COMPONENTS

FIELD OF THE INVENTION

This invention relates generally to knee prosthesis tibial componentry having interchangeable components.

BACKGROUND

Fixed bearing knee prosthesis comprises a metallic tibial tray to which a polymeric bearing insert is fixed. The bearing insert comprises lateral and medial articular surfaces for corresponding condyles of a femoral component.

As highly conforming articular geometries are desirous, especially for medial-pivot inserts, interfaces exist that allow for the interchange of bearing inserts for optimising femoral conformity, such as that which is disclosed in U.S. Pat. No. 7,628,818 B2 (Hazebrouck).

However, degradation from typically 2-25 μm cyclic axial load micromotion in the interface shear plane is problematic and "back side wear" is commonly observed.

Furthermore, posterior stabilised designs with rollback forcing cam post mechanisms can create significant force in the shear plane at certain flexion angles which exacerbates cyclic micromotion.

The present invention seeks to provide a knee prosthesis tibial bearing insert and tray interface, which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art.

SUMMARY OF THE DISCLOSURE

The present knee prosthesis tibial componentry comprises a bearing insert defining a superior condyle articular surface and a planar inferior bearing surface. A tray having a platform defining a superior bearing surface and an inferior stem engages the insert.

The tray comprises a quadrant of retention buttresses having anterior and posterior buttresses, each extending superiorly with respect to the superior bearing surface and extending in from a peripheral edge of the superior bearing surface. The insert comprises a quadrant of respective spaced apart retention recesses having anterior and posterior recesses, each recessed superiorly with respect to the inferior bearing surface and extending in from a peripheral edge of the inferior bearing surface.

The buttresses and recesses define bearing faces that tightly bear against each other in a transverse plane both mediolaterally and anteroposteriorly to retain the insert to the tray.

The buttresses are spaced apart mediolaterally to allow an anteroposterior channel therebetween across the platform to accommodate a continuous anteroposterior portion of the insert and to allow a posterior bearing surface between the posterior buttresses and the buttresses are spaced apart anteroposteriorly to allow a mediolateral channel across the platform to accommodate a continuous mediolateral portion of the insert.

The quadrant of buttresses at outer edges of the platform maximise surface area of the bearing surfaces to reduce per unit area loading and therefore polyethylene wear debris.

Furthermore, the quadrant of buttresses restrain micromotion, including rotational micromotion, without substantially intruding underneath the insert as do the tray formations of Hazebrouck, thereby not similarly adversely limiting articular surface geometry and minimum bearing thickness requirements.

Furthermore, the anteroposterior channel between the buttresses allows for the continuous mediolateral portion right across the tibial bearing insert which reduces mediolateral deformation thereof and micromotion with respect to the tibial tray. Similarly, the mediolateral channel of the buttresses allows for the continuous anterior posterior portion right across the tibial bearing insert for similar effect.

Furthermore, the mediolateral spacing between the posterior buttresses allows for a posterior bearing surface therebetween which increases posterior contact bearing surface area to reduce back side wear.

Preferably, the bearing faces have inner portions which bear predominantly mediolaterally to reduce mediolateral posterior micromotion. Preferably these inner portions are parallel with respect to an anteroposterior axis to maximise mediolateral bearing force vectors. Preferably these inner portions are planar to aid tight tolerance manufacturing to reduce micromotion. Further preferably, the bearing faces of the anterior buttresses and recesses may be similarly arranged to reduce mediolateral anterior micromotion.

Further preferably, bearing faces of anterior and posterior buttresses may comprises mid portions which oppose each other predominantly anteroposteriorly to reduce anteroposterior micromotion. Furthermore, these mid portions are preferably parallel with respect to a mediolateral axis to maximise anteroposterior force vector components. Furthermore, these mid portions are preferably planar to spread anteroposterior bearing force therealong and for aiding tight tolerance manufacturing.

Further preferably, the bearing faces of the buttresses may comprise outer portions which are radially orientated (i.e. between anteroposterior and mediolateral axes) to resist rotation force about a superior/inferior axis to reduce micromotion.

The componentry may comprise tibial tray and inserts of graduated sizing but wherein spacing between the inner and mid portions of the bearing faces remains consistent for interchangeability.

According to one aspect, there is provided knee prosthesis tibial componentry comprising: a bearing insert defining a superior condyle articular surface and a planar inferior bearing surface; and a tray having: a platform defining a superior bearing surface, and an inferior stem, wherein the tray comprises a quadrant of retention buttresses having anterior and posterior buttresses, each extending superiorly with respect to the superior bearing surface and extending in from a peripheral edge of the superior bearing surface, wherein the insert comprises a quadrant of spaced apart retention recesses having anterior and posterior recesses, each recessed superiorly with respect to the inferior bearing surface and extending in from a peripheral edge of the inferior bearing surface, wherein the buttresses and recesses define bearing faces that tightly bear against each other in a transverse plane both mediolaterally and anteroposteriorly to retain the insert to the tray, wherein the buttresses are spaced apart mediolaterally to allow an anteroposterior channel therebetween across the platform to accommodate a continuous anteroposterior portion of the insert and to allow a posterior bearing surface between the posterior buttresses; and wherein the buttresses are spaced apart anteroposteriorly to allow a mediolateral channel across the platform to accommodate a continuous mediolateral portion of the insert.

The anteroposterior channel may have a width of at least 10% of mediolateral extent of the superior bearing surface.

The mediolateral channel may have a width of at least 20% of anteroposterior extent of the superior bearing surface.

Bearing faces of the posterior buttresses and recesses may comprise elongate inner portions that bear predominantly mediolaterally against each other in the transverse plane.

Bearing faces of the anterior buttresses and recesses may comprise elongate inner portions that bear predominantly mediolaterally against each other in the transverse plane.

The inner portions may be planar.

The inner portions may be parallel with respect to an anteroposterior axis.

Bearing faces of the posterior buttresses and recesses may comprise elongate mid portions that bear predominantly anteroposteriorly in the transverse plane.

Bearing faces of anterior buttresses and recesses may comprise elongate mid portions that bear predominantly posteriorly in the transverse plane.

The mid portions may be planar.

The mid portions may be parallel with respect to a mediolateral axis.

Bearing faces of posterior buttresses and recesses may comprise elongate outer portions and wherein the elongate outer portions may be orientated radially between anteroposterior and mediolateral axes.

Bearing faces of anterior buttresses and recesses may comprise elongate outer portions and wherein the elongate outer portions may be orientated radially between anteroposterior and mediolateral axes.

The outer portions may be planar.

Posterior bearing faces may be angled with respect to a frontal plane to engage over oppositely angled bearing faces of posterior recesses.

The anterior recesses may comprise deflectable clips which engage under corresponding retention edges of the posterior buttresses.

Bearing faces of anterior buttresses and recesses may comprise elongate outer portions and wherein the elongate outer portions may be orientated radially between anteroposterior and mediolateral axes and wherein the deflectable clips and posterior buttresses may be arranged along the elongate outer portions.

An inferior edge of each clip may be chamfered.

Each clip may extend to an edge of the insert.

The insert comprises a recess at an edge of the inferior bearing surface between the anterior recesses.

The componentry may further comprise a further insert of differing dimensions as compared to the insert except for mediolateral and anteroposterior spacing between the bearing faces.

Other aspects of the invention are also disclosed.

BRIEF DESCRIPTION OF THE DRAWINGS

Notwithstanding any other forms which may fall within the scope of the present invention, preferred embodiments of the disclosure will now be described, by way of example only, with reference to the accompanying drawings in which.

DESCRIPTION OF EMBODIMENTS

Knee prosthesis tibial componentry 100 comprises an insert 101 of polymeric material. One such polymeric material is polyethylene such as ultrahigh molecular weight polyethylene (UHMWPE).

The componentry 100 comprises a tibial tray 102 of biocompatible metal, such as a cobalt chrome alloy.

Figure 1:
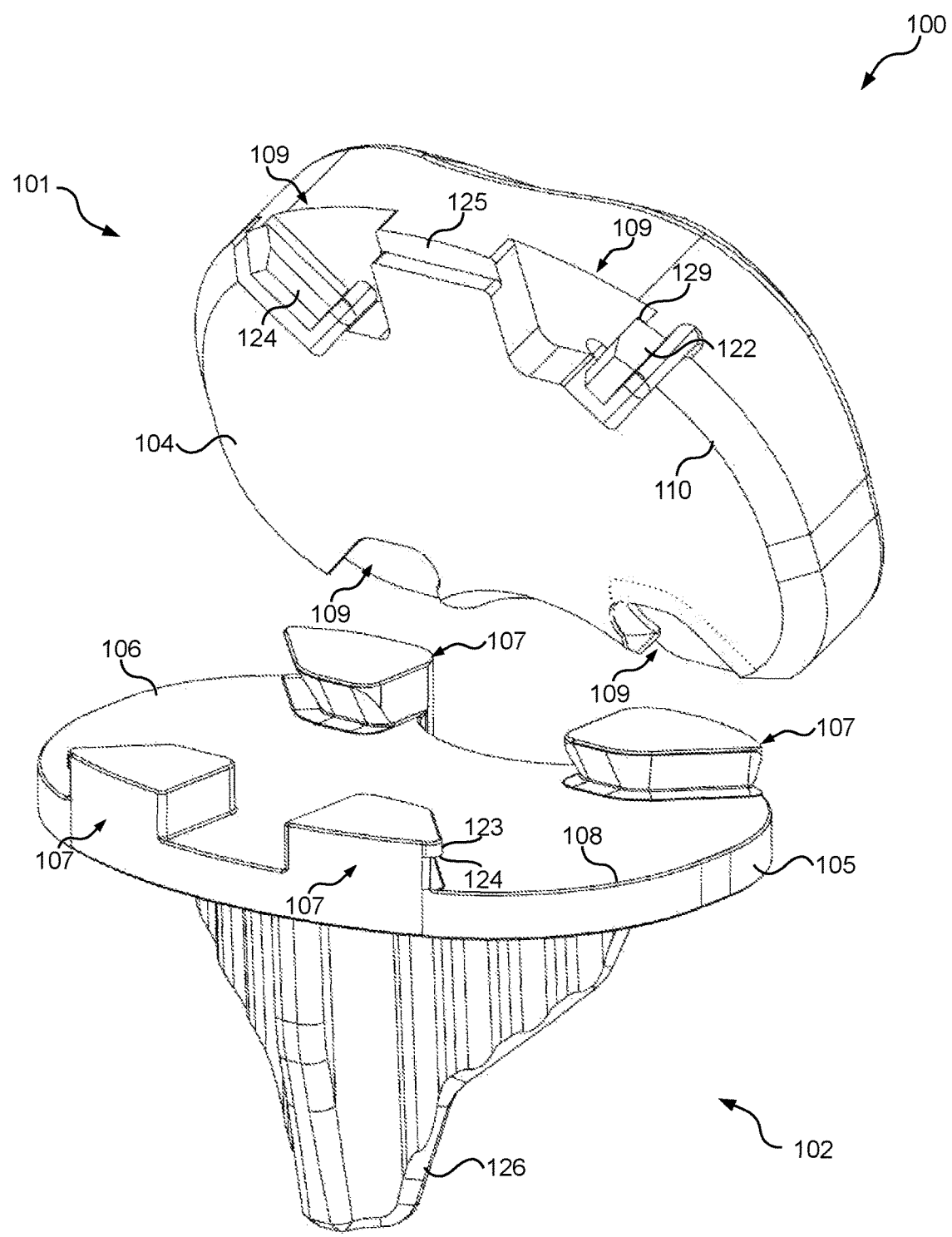
FIG. 1 shows knee prosthesis tibial componentry in accordance with an embodiment.
Figures 4A, 4B:
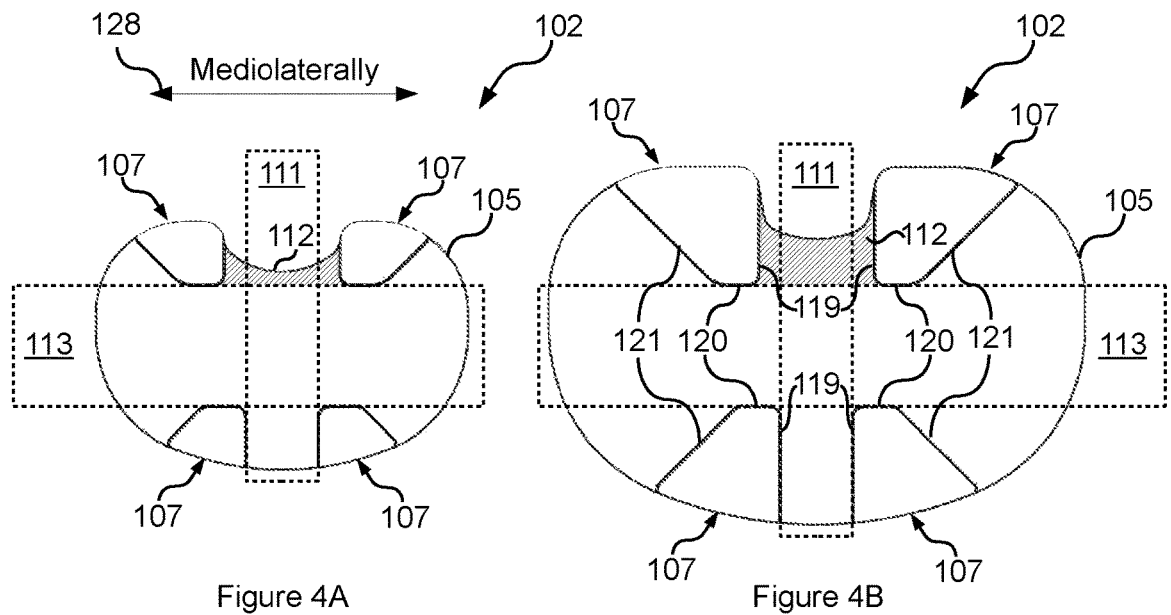
FIG. 4 shows a topside plan view of trays of differing sizes of the componentry.
Figures 5A, 5B:
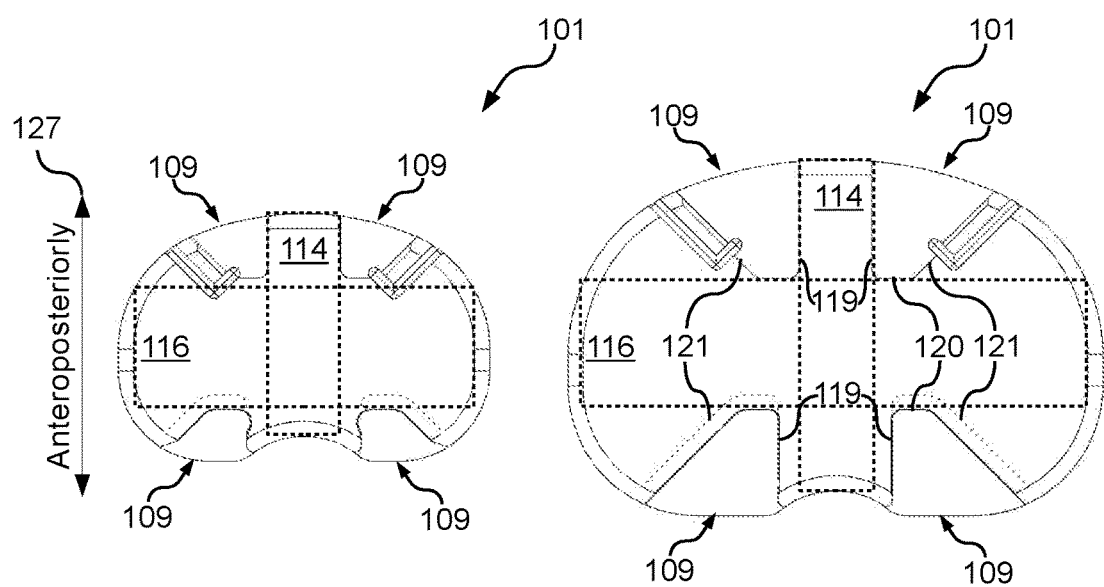
FIG. 5 shows an underside plan views of inserts of differing sizes of the componentry.
Figure 6:
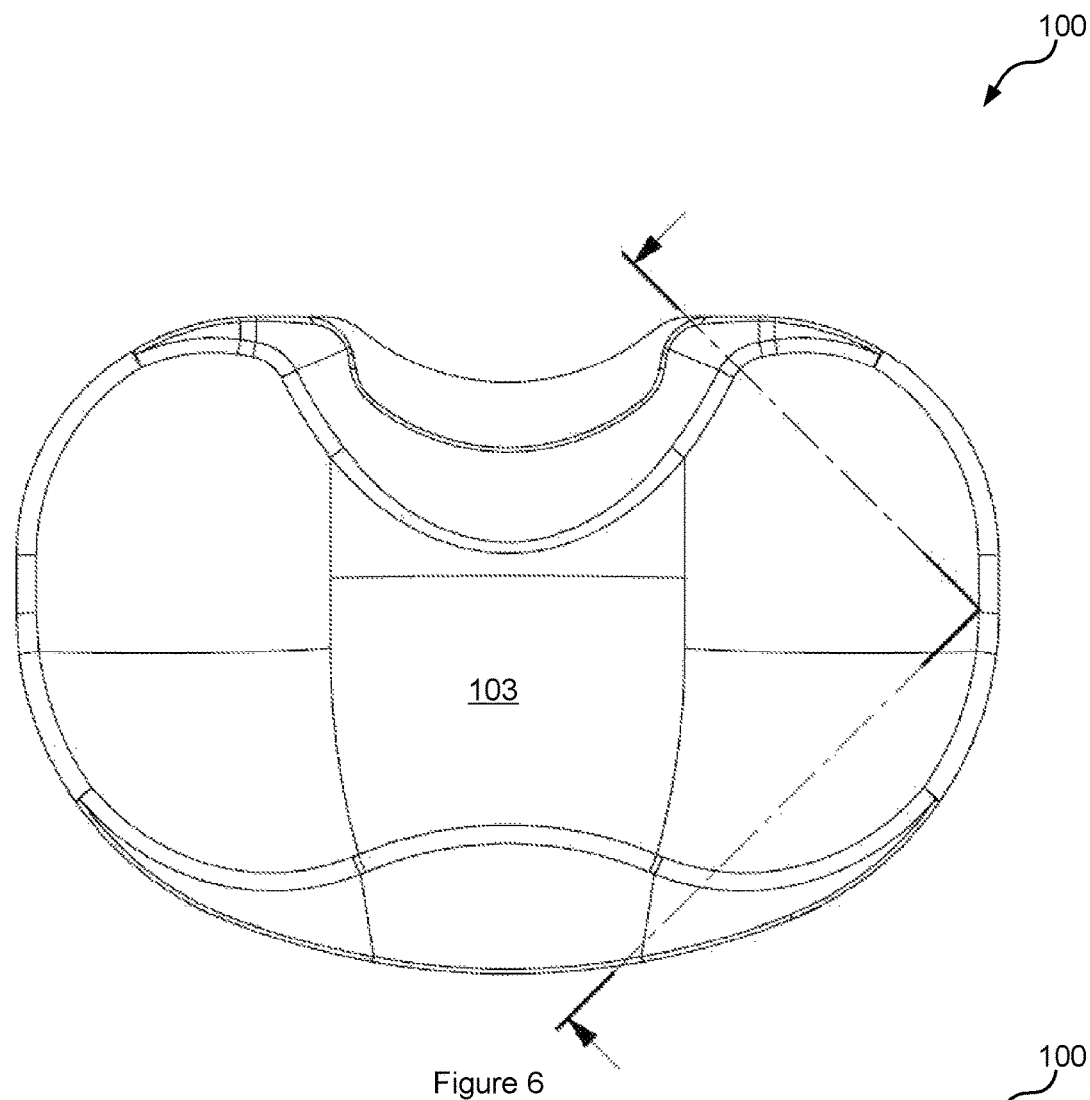
FIG. 6 shows a top plan view of the insert engaged to the tray of the componentry.

With reference to the orientation of FIG. 1 superior and derivatives thereof refer to the top or upper and inferior and derivatives thereof to the bottom or lower. Medial and derivatives thereof refer to the left and lateral and derivatives thereof refer to the right. Mediolateral refers to left to right or sideways across as illustrated in FIG. 4A. Anterior refers to the front or forward and posterior refers to the back or backward and anteroposterior refers to along or from front to back as illustrated in FIG. 5A. Inner and derivatives thereof refer to in towards the centre of the componentry 100 and outer and derivatives thereof refer to out from the centre of the componentry 100.

The insert 100 defines a superior condyle articular surface 103 and a planar inferior bearing surface 104 in the transverse plane. The articular surfaces 103 may be suited for medial-pivot, posterior-stabilised, cruciate ligament-retaining prosthesis or ultra-congruent cruciate ligament-retaining prosthesis in various embodiments.

The tibial tray 102 has a platform 105 defining a superior planar bearing surface 106 in the transverse plane and an inferior stem 126 for intermedullary retention.

The tibial tray 102 comprises a quadrant of spaced apart retention buttresses 107 each extending superiorly with respect to the superior bearing surface 106. Each retention buttress 107 extends in from a peripheral edge 108 of the superior bearing surface 106 of the platform 105.

The insert 101 comprises a quadrant of retention recesses 109 conforming in location to respective buttresses 107. The retention recesses 109 each are recessed superiorly with respect to the inferior bearing surface 104. Each retention recess 109 similarly extends in from a peripheral edge 110 of the insert 101.

The buttresses 107 act across the transverse plane to engage the respective recesses 109 to fix the insert 101 to the tray 102.

With reference to FIGS. 4 and 5, the buttresses 107 are mediolaterally spaced to allow an anteroposterior channel 111 across the platform 105 to accommodate a continuous anteroposterior portion 114 of the insert 101.

Furthermore, the mediolateral spacing of the posterior buttresses 107 allow for a posterior bearing surface 112 between the posterior buttresses 107.

Furthermore, the anteroposterior spacing of the buttresses 107 allow mediolateral channel 113 between the buttresses 107 to accommodate a continuous mediolateral portion 116 of the insert 101.

The anteroposterior channel 111 preferably has a width of at least 10% of the mediolateral extent of the platform 105. The mediolateral channel 113 preferably has a width of at least 20% of the anteroposterior extent of the platform 105.

The buttresses 107 and the recesses 109 define bearing faces that tightly bear oppositely in the transverse plane to hold the insert 101 to the tray 102.

With reference to FIGS. 4 and 5 bearing faces of at least one of anterior and posterior buttresses 107 and recesses 109 may comprise elongate inner portions 119 that bear predominantly mediolaterally against each other. "Predominantly mediolaterally" should be construed in that the mediolateral force vector component exceeds the anteroposterior force vector component exerted by the inner portions 119. Preferably the inner portions 119 are parallel with respect to an anteroposterior axis 127. Preferably, the inner portions 119 are planar.

The bearing faces of at least one of anterior and posterior buttresses 107 and recesses 109 may further comprise elongate mid portions 120 that bear against each other predominantly anteroposteriorly. Similarly, "predominantly anteroposteriorly" should be construed in that the anteroposterior force vector component exceeds the mediolateral force vector component exerted by the mid portions 120. Preferably the mid portions 120 are parallel with respect to a mediolateral axis 128. Preferably the mid portions 120 are planar.

The bearing faces of at least one of anterior and posterior buttresses 107 and recesses 109 may comprise elongate outer portions 121. Preferably the outer portions are radially orientated (i.e. orientated between anteroposterior 127 and mediolateral 128 axes).

Figure 7:
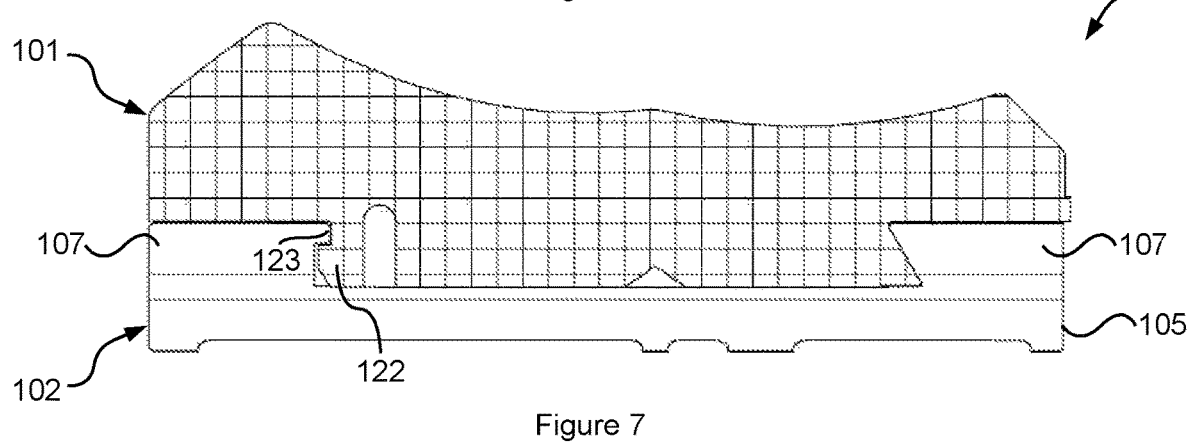
FIG. 7 shows a side view of the cross-section of FIG. 6.

As best seen in FIG. 7, the bearing faces of the posterior buttresses 107 may be angled with respect to the frontal plane to engage over oppositely angled bearing faces of posterior recesses 109.

Anterior recesses 109 may comprise retention clips 122 which engage over respective edges 123 of anterior buttresses 107.

Figure 8:
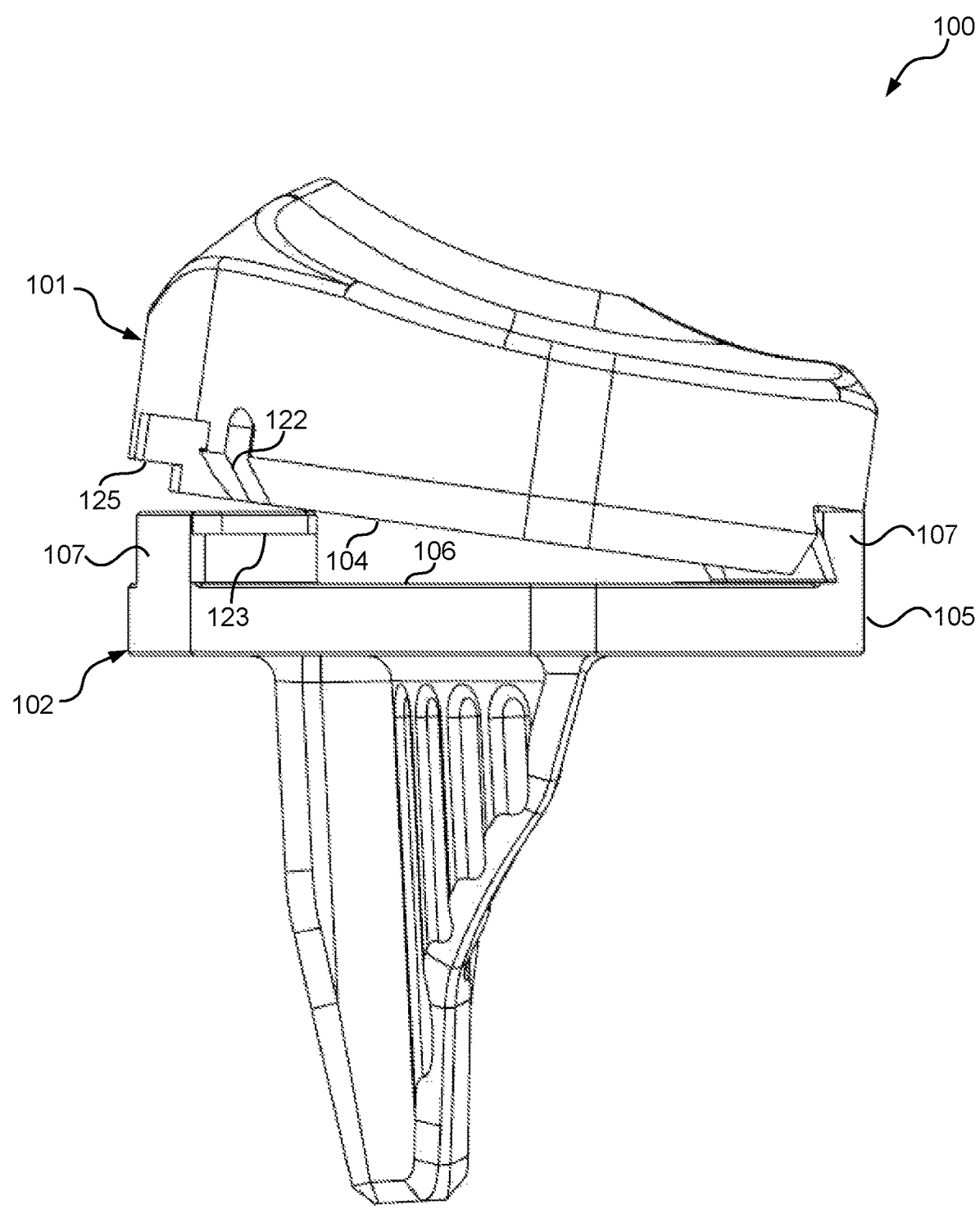
FIG. 8 illustrates the insert engaging the tray.

The angled bearing faces and retention clips 122 allow the insert 101 to engage the tray 102 in the manner shown in FIG. 8.

Preferably the clips 122 and edges 123 are located on the outer portions 121 of the bearing faces.

The clips 122 may comprise a superior edge 129 that engages under a corresponding inferior edge 124 of the retention edge 123. The clips 122 may comprise an inferior chamfer 124 to aid deflection over the retention edge 123 when the insert 101 is pressed onto the tray 102.

The clips 122 may accessibly extend to edges of the insert 101 so as to be accessible for insertion of a screwdriver or the like between the clips 122 and the retention edge 123 for disconnection.

The insert 101 may comprise a recess 125 between the anterior recesses 109 for insertion of a lever for prising the insert 101 from the tray 105.

Figure 2:
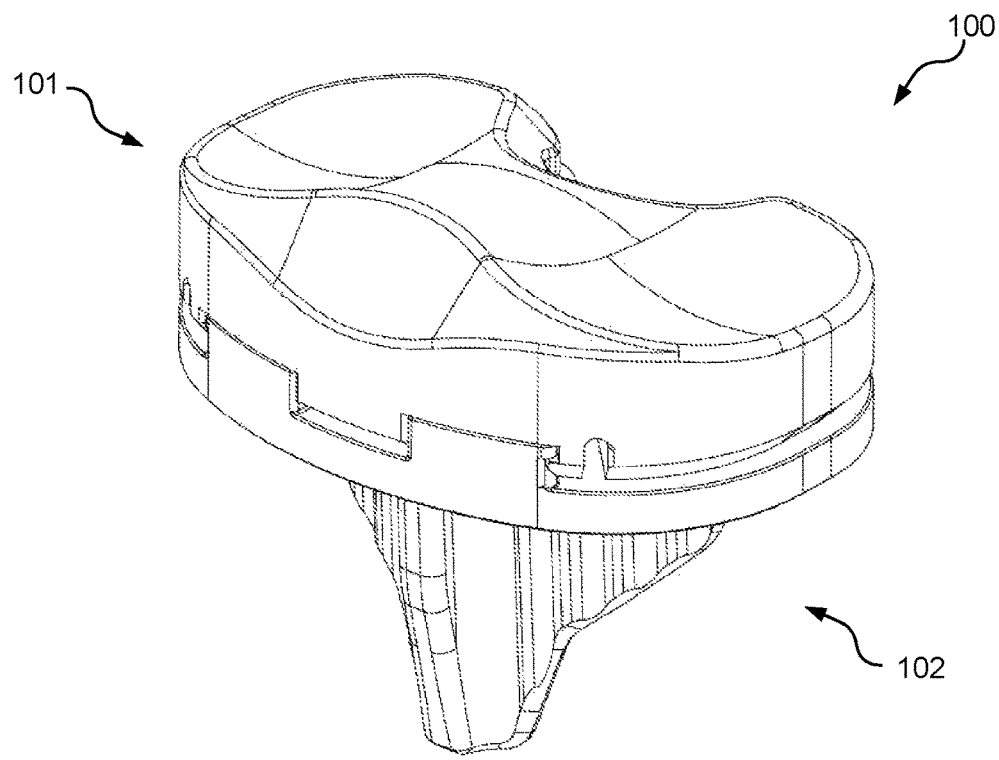
FIGS. 2 and 3 show inserts of differing sizes engaged to a tray of the componentry.
Figure 3:
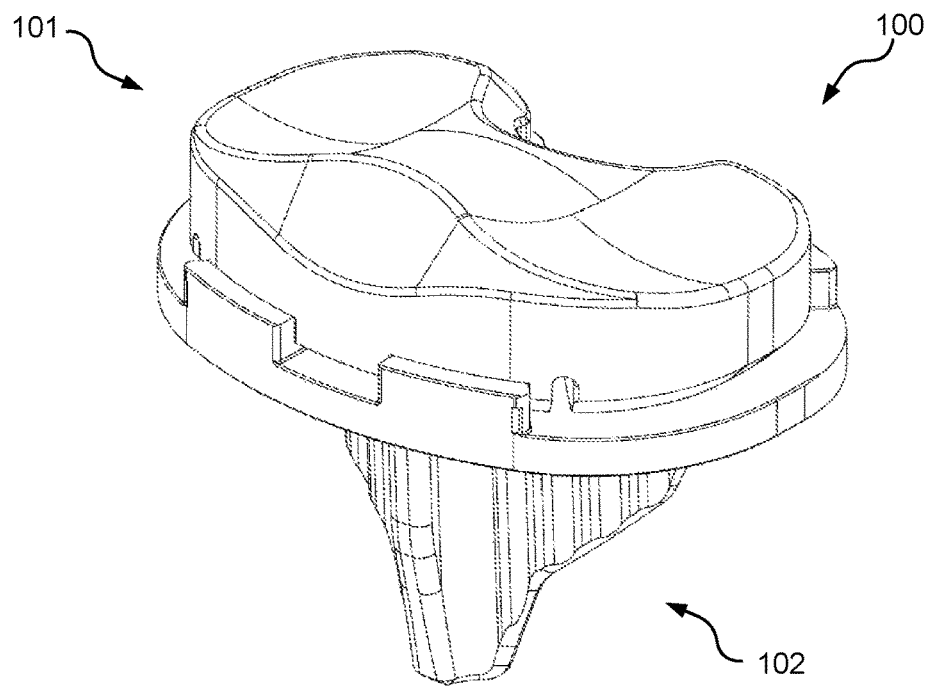

FIGS. 2 and 3 illustrate inserts 101 of differing dimensions engaged to the tray 102 wherein the mediolateral and anteroposterior spacing between the bearing faces of the buttresses 107 and the recesses 109 remains consistent for interchangeability.

The foregoing description, for purposes of explanation, used specific nomenclature to provide a thorough understanding of the invention. However, it will be apparent to one skilled in the art that specific details are not required in order to practise the invention. Thus, the foregoing descriptions of specific embodiments of the invention are presented for purposes of illustration and description. They are not intended to be exhaustive or to limit the invention to the precise forms disclosed as obviously many modifications and variations are possible in view of the above teachings. The embodiments were chosen and described in order to best explain the principles of the invention and its practical applications, thereby enabling others skilled in the art to best utilize the invention and various embodiments with various modifications as are suited to the particular use contemplated. It is intended that the following claims and their equivalents define the scope of the invention.

The term "approximately" or similar as used herein should be construed as being within 10% of the value stated unless otherwise indicated.

The invention claimed is:

1. Knee prosthesis tibial componentry comprising:
   a bearing insert defining a superior condyle articular surface and a planar inferior bearing surface; and
   a tray having a platform defining a superior bearing surface and an inferior stem,
   wherein the tray comprises a quadrant of retention buttresses having anterior and posterior buttresses, each extending superiorly with respect to the superior bearing surface and extending in from a peripheral edge of the superior bearing surface,
   wherein the insert comprises a quadrant of spaced apart retention recesses having anterior and posterior recesses, each recessed superiorly with respect to the inferior bearing surface and extending in from a peripheral edge of the inferior bearing surface,
   wherein the buttresses and recesses define bearing faces that tightly bear against each other in a transverse plane both mediolaterally and anteroposteriorly to retain the insert to the tray,
   wherein the buttresses are spaced apart mediolaterally to allow an anteroposterior channel therebetween across the platform to accommodate a continuous anteroposterior portion of the insert and to allow a posterior bearing surface between the posterior buttresses; and
   wherein the buttresses are spaced apart anteroposteriorly to allow a mediolateral channel across the platform to accommodate a continuous mediolateral portion of the insert.

2. Componentry as claimed in claim 1, wherein the anteroposterior channel has a width of at least 10% of mediolateral extent of the superior bearing surface.

3. Componentry as claimed in claim 1, wherein the mediolateral channel has a width of at least 20% of anteroposterior extent of the superior bearing surface.

4. Componentry as claimed in claim 1, wherein bearing faces of the posterior buttresses and recesses comprise elongate inner portions that bear predominantly mediolaterally against each other in the transverse plane.

5. Componentry as claimed in claim 1, wherein bearing faces of the anterior buttresses and recesses comprise elongate inner portions that bear predominantly mediolaterally against each other in the transverse plane.

6. Componentry as claimed in claim 4 or 5, wherein the inner portions are planar.

7. Componentry as claimed in claim 6, wherein the inner portions are parallel with respect to an anteroposterior axis.

8. Componentry as claimed in claim 1, wherein bearing faces of the posterior buttresses and recesses comprise elongate mid portions that bear predominantly anteroposteriorly in the transverse plane.

9. Componentry as claimed in claim 1, wherein bearing faces of anterior buttresses and recesses comprise elongate mid portions that bear predominantly posteriorly in the transverse plane.

10. Componentry as claimed in claim 8 or 9, wherein the mid portions are planar.

11. Componentry as claimed in claim 10, wherein the mid portions are parallel with respect to a mediolateral axis.

12. Componentry as claimed in claim 1, wherein bearing faces of posterior buttresses and recesses comprise elongate outer portions and wherein the elongate outer portions are orientated radially between anteroposterior and mediolateral axes.

13. Componentry as claimed in claim 1, wherein bearing faces of anterior buttresses and recesses comprise elongate outer portions and wherein the elongate outer portions are orientated radially between anteroposterior and mediolateral axes.

14. Componentry as claimed in claim 12 or 13, wherein the outer portions are planar.

15. Componentry as claimed in claim 1, wherein posterior bearing faces are angled with respect to a frontal plane to engage over oppositely angled bearing faces of posterior recesses.

16. Componentry as claimed in claim 1, wherein the anterior recesses comprise deflectable clips which engage under corresponding retention edges of the posterior buttresses.

17. Componentry as claimed in claim 16, wherein bearing faces of anterior buttresses and recesses comprise elongate outer portions and wherein the elongate outer portions are orientated radially between anteroposterior and mediolateral axes and wherein the deflectable clips and posterior buttresses are arranged along the elongate outer portions.

18. Componentry as claimed in claim 16, wherein an inferior edge of each clip is chamfered.

19. Componentry as claimed in claim 16, wherein each clip extends to an edge of the insert.

20. Componentry as claimed in claim 1, wherein the insert comprises a recess at an edge of the inferior bearing surface between the anterior recesses.

21. Componentry as claimed in claim 1, further comprising a further insert of differing dimensions as compared to the insert except for mediolateral and anteroposterior spacing between the bearing faces.

\* \* \* \* \*